(12) United States Patent
Meek et al.

(10) Patent No.: US 9,492,131 B2
(45) Date of Patent: Nov. 15, 2016

(54) MOTOR ASSISTED MANUALLY CONTROLLED MOVEMENT ASSEMBLY, X-RAY SYSTEM COMPRISING THE SAME, METHOD AND USE

(75) Inventors: Gerrit Jan Meek, Eindhoven (NL); Ravindra Bhat, Eindhoven (NL); Antonius Maria Rijken, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 878 days.

(21) Appl. No.: 13/319,343

(22) PCT Filed: Apr. 19, 2010

(86) PCT No.: PCT/IB2010/051697
§ 371 (c)(1),
(2), (4) Date: Jan. 11, 2012

(87) PCT Pub. No.: WO2010/128417
PCT Pub. Date: Nov. 11, 2010

(65) Prior Publication Data
US 2012/0106701 A1 May 3, 2012

(30) Foreign Application Priority Data

May 8, 2009 (EP) .................................... 09159808

(51) Int. Cl.
*A61B 6/00* (2006.01)
*H05G 1/02* (2006.01)
(Continued)

(52) U.S. Cl.
CPC ........... *A61B 6/4482* (2013.01); *A61B 6/4476* (2013.01); *A61B 6/0457* (2013.01); *A61B 6/4405* (2013.01); *A61B 6/4441* (2013.01);
(Continued)

(58) Field of Classification Search
CPC ............ H05G 1/02; H05G 1/08; A61B 6/44; A61B 6/4405; A61B 6/4476; A61B 6/4482
USPC ........ 378/4–20, 91, 189, 193–198, 204, 210
See application file for complete search history.

(56) References Cited

U.S. PATENT DOCUMENTS 3,866,048 A * 2/1975 Gieschen et al. ................ 378/91
3,986,090 A * 10/1976 Hecker et al. ................. 318/488
(Continued)

FOREIGN PATENT DOCUMENTS

CN 201227280 Y 4/2009
DE 4237013 C2 10/1996
(Continued)

OTHER PUBLICATIONS

PT Design Magazine, "Direct Drive Motors", Nov. 1999.*
(Continued)

*Primary Examiner* — Anastasia Midkiff (57) ABSTRACT

A motor assisted movement assembly 2 is provided comprising a motor arrangement 3, which motor arrangement 3 may assist a manually controlled movement of a first structural element 5 relative to a second structural element 6. A motor element 3*a* of the motor arrangement 3 is adapted to detect a manual indication of a desired movement of the second structural element 6 relative to the first structural element 5 with the motor arrangement 3 being adapted to assist, e.g. support the movement by providing an additional force.

32 Claims, 9 Drawing Sheets (51) Int. Cl.
   *H05G 1/08* (2006.01)
   *A61B 6/04* (2006.01)
(52) U.S. Cl.
   CPC ........... *A61B 6/4464* (2013.01); *A61B 6/5276* (2013.01); *H05G 1/02* (2013.01); *H05G 1/08* (2013.01); *Y10T 74/19051* (2015.01)

(56) References Cited

U.S. PATENT DOCUMENTS

| | | | |
|---|---|---|---|
| 4,021,715 A * | 5/1977 | Von Hacht et al. | 318/628 |
| 4,107,590 A | 8/1978 | Pury et al. | |
| 4,163,929 A | 8/1979 | Janu et al. | |
| 4,208,586 A * | 6/1980 | Craig et al. | 378/189 |
| 4,276,490 A * | 6/1981 | Saldinger | 310/184 |
| 4,367,532 A * | 1/1983 | Crum et al. | 700/260 |
| 4,492,526 A * | 1/1985 | Hartwig | F04C 28/08 417/45 |
| 4,847,543 A * | 7/1989 | Fellinger | 318/628 |
| 6,302,226 B1 * | 10/2001 | Kanno et al. | 180/6.5 |
| 6,320,336 B1 * | 11/2001 | Eguchi | 318/139 |
| 6,409,382 B1 * | 6/2002 | Akutsu et al. | 378/198 |
| 6,668,692 B1 * | 12/2003 | Thiele et al. | 83/74 |
| 7,175,346 B2 * | 2/2007 | Heinze et al. | 378/197 |
| 7,566,171 B2 * | 7/2009 | Fuhrmann | 378/197 |
| 2005/0100134 A1 | 5/2005 | Bauer | |
| 2005/0117710 A1 | 6/2005 | Heinze et al. | |
| 2006/0104496 A1 * | 5/2006 | Arenson | A61B 6/542 382/132 |
| 2006/0153340 A1 * | 7/2006 | Engstrom et al. | 378/197 |
| 2006/0258932 A1 | 11/2006 | Narayanasamy | |
| 2007/0078534 A1 * | 4/2007 | Boomgaarden | 700/63 |
| 2007/0194255 A1 * | 8/2007 | Garcia | A61L 2/10 250/504 R |
| 2007/0200396 A1 | 8/2007 | Baumann et al. | |
| 2008/0061252 A1 * | 3/2008 | Garcia | A61L 2/10 250/504 H |
| 2012/0032084 A1 * | 2/2012 | Sapp | H02K 41/025 250/360.1 |

FOREIGN PATENT DOCUMENTS

| | | |
|---|---|---|
| JP | 54127697 A | 10/1979 |
| JP | 61224012 A | 10/1986 |
| JP | 11070102 A | 3/1999 |
| JP | 2000201909 A | 7/2000 |
| JP | 2008126073 A | 6/2008 |

OTHER PUBLICATIONS

Prokop, Libor, et al., "3-Phase BLDC Motor Control with Sensroless Back-EMF ADC Zero Crosing Detection using 56F80x (Rev. 3)", Nov. 2005, Freescale Semiconductor, pp. 1-60.*
English Translation for JP 61224012 A (Previously submitted in Japanese by Applicant, in IDS filed Feb. 12, 2016).*

* cited by examiner

MOTOR ASSISTED MANUALLY CONTROLLED MOVEMENT ASSEMBLY, X-RAY SYSTEM COMPRISING THE SAME, METHOD AND USE

TECHNICAL FIELD OF THE INVENTION

The present invention relates to X-ray generating technology in general.

More particularly, the present invention relates to X-ray systems, mobile X-ray systems, C-arc systems for obtaining an X-ray image of an object.

In particular, it relates to the movement and the positioning of an X-ray system relative to the object to be examined.

BACKGROUND OF THE INVENTION

X-ray systems are well-known in the art for diagnostic and therapeutic purposes including X-ray image acquisition of an object to be examined, e.g. a region of interest of a living body.

X-ray systems for acquiring X-ray images regularly comprise an X-ray generating device, e.g. an X-ray, tube and an X-ray detector arranged and operatively coupled for the acquisition of X-ray images of an object to be examined. The X-ray generating device and the X-ray detector are arranged on opposite sides of the object facing towards each other. X-radiation emanating from the X-ray generating device is emitted in the direction of the X-ray detector, thus penetrating the object to be examined and consequently generating an X-ray image of the object within the X-ray detector.

Both the X-ray generating device and the X-ray detector are regularly rigid, heavy elements of a substantial weight. Thus, for moving the X-ray generating device and/or the X-ray detector about the object to be examined, e.g. for the acquisition X-ray images of different orientation, a force has to be applied to the X-ray generating device and/or the X-ray detector, which regularly may not be considered to be neglectable.

SUMMARY OF THE INVENTION

Thus, there may be a need for an assisted, however controlled movement of individual elements or devices of an X-ray system with reduced force requirements and increased positioning accuracy.

In the following, a motor assisted movement assembly, an X-ray system, a method of motor assisted movement as well as the use of a motor assisted movement assembly according to the independent claims are provided.

According to an exemplary embodiment of the present invention, a motor assisted movement assembly is provided, comprising a first structural element, a second structural element and a motor arrangement comprising a motor element. The first structural element and the second structural element are movable relative to each other with the motor arrangement being arranged at the first structural element. The second structural element is adapted to receive a manual indication of a desired movement of the second structural element relative to the first structural element. The motor arrangement is adapted to assist the movement of the second structural element relative to the first structural element in accordance with the manual indication. The motor element is adapted to detect the manual indication.

According to a further exemplary embodiment of the present invention, an X-ray system is provided, comprising an X-ray generating device, an X-ray detector and a motor assisted movement assembly. The X-ray generating device and the X-ray detector are operatively coupled and arranged for the acquisition of X-ray images of an object to be examined with the motor assisted movement assembly being adapted for moving at least one of the X-ray generating device and the X-ray detector about the object.

According to a further exemplary embodiment of the present invention, a method for motor assisted movement is provided, comprising the steps of detecting in a motor element a manual indication of a desired movement of a second structural element relative to a first structural element and the assisting the desired movement.

According to a further exemplary embodiment of the present invention, a motor assisted movement assembly is used in at least one of an X-ray system, a mobile X-ray system, a C-arc system and a patient support system.

The present invention may be seen as improving the control performance and adding enhanced functionality to manually controlled movements of a first structural element relative to a second structural element.

For example, in an interoperative scenario, an X-ray acquisition system, like for example a C-arc is employed. An operator, e.g. an X-ray technician, is required to acquire relevant images for, e.g. a surgeon before, during and after an operation. Since a C-arc only acquires two-dimensional images of a defined plane of a region of interest of an object, it may be necessary to move the C-arc, at least its C-bow element, or to realign the C-arc for the acquisition of an X-ray image of a different plane of view.

Also, space requirements or space limitations during an operation may require the positioning of the C-arc system away from the operating table when no image is to be acquired and subsequently moving the C-arc system in and out of the operating field when an image is to be acquired.

Since a C-arc regularly comprises a substantial weight, the relocation of at least one of the X-ray generating device and the X-ray detector may be tedious duty.

Furthermore, when moving the C-arc, it may be required to realign the X-ray detector and the X-ray generating device in a defined position used for a previous image acquisition, in particular to obtain matching subsequent X-ray images, e.g. after a defined part of a surgical procedure.

Thus, a motor assisted manually controlled movement of individual elements of the X-ray system or the X-ray system as a whole may be beneficial.

In particular, performance improvements may exist by motor systems during a manually controlled movement of a mechanically balanced system. An operator may initiate a desired movement, e.g. the rotation of X-ray generating device and/or the X-ray detector about an axis. This initiated movement or indication of movement may be determined and a suitably arranged motor may add an overlaying or additional force to decrease the feeling of friction and mass of the elements to be moved, thus assisting the movement while being manually controlled by the initiated movement of the operator/the indication of movement. In particular, a manual control element, e.g. a hand grip, which may not comprise sensors, switches or the like, may be employed for providing the indication of movement. However, a dedicated manual control element may not be required at all but may be beneficial. An according manual control element may in particular provide for reception of manual control input and may be suitable for receiving an appropriate input for all feasible movements or movement directions.

Further functions may be programmable arret stops for the guidance to preferred or preset positions, which may be stored in control applications or programs may be provided, e.g. for relocating the X-ray system in a defined and/or previously used position for the acquisition of images. Also, individual user profiles with different, individual levels of motor assistance may be implemented.

A direct drive behavior of a direct drive motor technology, e.g. a drive without the requirements of a separate gear box with a specific gear transmission ratio may be employed, thus reducing the number of drive components of a drive train.

The direct drive principle may allow the implementation of different modes of operation, e.g. a drive operation mode, a clutch operation mode and a break operation mode.

The drive operation mode may allow employing the motor assisted manually controlled movement as previously described.

By an interruption of supply power from the motor element, a substantially free running motor element may be obtained, which may be considered to be essentially free running without requiring further applied forces over the non-assisted manual movement of the structural element. An according operation may be referred to as the clutch operation mode.

In a break operation mode, the X-ray generating device and/or the X-ray detector may stop in a predefined position and may even be kept in said position by the motor counteracting, possibly unintentionally applied forces to, e.g. the C-arc or at least the C-bow element.

An according motor element may be a brushed or a brushless motor element. A brushless motor may provide good control behavior at high torques and low speeds including zero speed. Consequently, low gearing drive trains or direct drive trains may be employed, thus resulting in a highly efficient transmission.

A further advantage of an essentially direct drive may be that the motor element current may be a good measure or indication for a respective torque at a defined load. A motion control element may be set to torque or current mode, where an applied torque to the motor is determined by a resulting motor current, being the basis for the motor assist functionality. In other words, the motor may determine what the operator is intending to do/which movement the operator is desiring and consequently the motion control element may react on a position feedback and may deliver by the motor element a part of the force that is required to move the X-ray system as desired.

Further functions like arret stops, preferred positioning and breaking may be achieved by substantially instantaneous switching, e.g. "on the fly switching", from torque mode to a speed or positioning mode, in which an absolute position of a first structural element and a second structural element, possibly comprising the X-ray generating device and/or the X-ray detector is determined. The position may also comprise a relative position of the first structural element and the second structural element to each other.

A further issue of the motor assist functionality may be the safety aspect. In known systems, a motor driven part around a patient may be controlled by means of a button under "dead man control", i.e. when the button is released the movement is stopped substantially immediately. Since a feature of the present invention may be seen as the omission of a dedicated actuating element, e.g. a switch or button for the control and initiation of a motor driven movement, further safety measures may have to be implemented. A safety measure may e.g. be limiting the torque and movement speed of the assisted movement to a level which requires a substantially constant force or indication of an operator. In case this constant force or indication is not present any more the movement may also be stopped essentially immediately. An according safety feature may meet the "single fault safety requirement", meaning that any single component failure or failure to provide the required constant force or indication shall lead to the shut down of a system in/to a safe state and prevent subsequent automatic operation until the respective problem has been corrected.

The present invention may particularly provide the following features.

A motor may assist manually controlled movements, thus motor assisted movements, may decrease the necessary handling forces to move and/or position the X-ray system with respect to an object to be examined to a low level, at least reducing handling forces substantially. These reduced handling forces may result in a faster and/or more accurate positioning of the X-ray system or X-ray beam.

A separate, dedicated "move enable" actuator, switch or button may not be required.

Furthermore, pre-programmed arret stops may be implemented. In other words, a preferred, predefined positioning of the X-ray system may be conveniently programmed and may be executed automatically. This may include a possibility or an option to revert, i.e. to move back, to previously used positions.

Also, motorized stop and hold/break functionality may be implemented. The motor element or the motor arrangement may be programmed to reduce handling forces, e.g. perceived moving mass and friction by a user, but may also limit the maximum speed of movement by employing velocity influenced damping or velocity dependent damping.

Different modes of operation, like e.g. drive mode, drive operation mode, clutch operation mode and/or break operation mode may be realized with a single component by programming the motor arrangement accordingly. However, there may always be the possibility to position the X-ray system manually, also or in particular when the motor element is not actuated. All of this may lead to a system that is inherently secure without the possibility of the system getting out of control of a user or operator.

Regularly, the motor arrangement of X-ray systems, in particular C-arc based X-ray systems for medical imaging, are based on a timing belt arrangement. The timing belt may be attached to one structural element with the motor element being arranged at the other structural element, which may be supposed to be movable relative to one another. For example, the timing belt of a C-arc system may run from one end of the C-bow element to the other end and may be mounted in particular with a heavy pretention to obtain sufficient drive stiffness.

A toothed drive wheel of the motor element is possibly locking/engaging with e.g. teeth of the timing belt, which is fed via at least two guide wheels from the C-bow to the motor element however, according to a further aspect of the present invention, a dual belt drive, i.e. a further embodiment of an Omega drive, may be employed.

Dual belt drives comprise two belts, e.g. both of which are toothed. One belt may be directly attached to the C-bow substantially along its entire length while the other belt is mounted with teeth to teeth mating, being further positioned at the motor element. As the motor shaft of the motor element rotates, the belt unmeshes on one side, in a vicinity of a first guide wheel and meshes on a second side arranged at a second guide wheel. The guide wheels or rollers ensure proper meshing without inducing tolerances. Thus, by actuating the motor element, the first structural element and the second structural element are movably relative to each other. The force/tension of the belt may be considered to exist only in a relatively small zone between the two guide wheels, substantially reducing the relevant belt length and contributes to stiffness being produced.

The parts of the belt arranged at the motor shaft, extending from the guide wheels or rollers to either side or end of the C-bow, may be considered to not contribute to the drive stiffness, thus are regularly not required to comprise a pretention comparable to that of a regular Omega drive. The dual belt drive may in particular provide a high stiffness of the drive arrangement even with low capacity belts and no or reduced pretention. Small belts may be employed which may result in a compact design. The absence or reduction of pretention may free the C-bow of any loading. Bearings may thus be small and compact, the possibility of using a small pitch may improve the drive accuracy and the stiffness of the belt, as seen by the motor element or motor arrangement may be considered to be constant over the entire stroke/maximum possible movement.

In the following, further exemplary embodiments of the present invention are described relating in particular to a motor assisted movement assembly. However, it is to be understood that these explanations also apply to the X-ray system comprising a motor assisted movement assembly, to the method of motor assisted movement and to the use of a motor assisted movement assembly.

It is explicitly noted, that arbitrary variations and interchanges of single or multiple features between claimed entities, in particular between embodiments relating to apparatus type claims, method type claims and use type claims, are conceivable and within the scope and disclosure of the present patent application.

According to a further exemplary embodiment of the present invention, the motor element may be adapted to detect a torque applied to the motor arrangement.

In other words, when, e.g. the manual control element, is employed for providing an indication of a desired movement, the indication may result in a translative or rotational force acting on the motor element, in particular a motor element shaft, in a way that may be seen as an attempt to rotate the shaft of the motor element, thus applying a torque to the motor element.

This attempted rotation of the motor element shaft may e.g. result in a current being produced within the motor element, which may be detected at the electrical connections of the motor element, e.g. by the motor itself or a successive control system. This produced current may thus be employed to detect a torque applied to the motor arrangement, possibly resulting in a defined reaction.

According to a further exemplary embodiment of the present invention, the motor arrangement may be a direct drive motor arrangement.

A direct drive motor arrangement may be understood as a motor arrangement which is substantially gear-free or transmission-free, thus the rotation is transmitted directly without the need for providing a transmission ratio, which in turn may require additional elements e.g. elements of a gear train or transmission train, to be moved, thus increasing the accuracy while reducing power requirements of the motor arrangement.

According to a further exemplary embodiment of the present invention, the direct drive motor arrangement is adapted to comprise a drive operation mode, a clutch operation mode and/or a break operation mode.

The drive operation mode may be interpreted as an operation mode where a motor assisted movement is provided. The clutch operation mode may be seen as an operation mode where a substantially free, unassisted, in particular manual movement of the first structural element relative to the second structural element is provided. In the clutch operation mode, substantially no power may be supplied to the motor arrangement/motor element. In a break operation mode, a defined position of the first structural element relative to the second structural element may be upheld, even with external, possibly unintentional forces acting on the structural elements. A break operation mode may in particular require determining an absolute position of the structural elements relative to one another. Also in the break operation mode, a motor assisted movement may be decelerated until a defined position has been reached, which position may subsequently be upheld, even while counteracting an additional external force.

According to a further exemplary embodiment of the present invention, the motor element is a brushless motor element.

A brushless motor element may be seen as a motor element which comprises an electronically controlled commutation system as opposed to a mechanical commutation system based on brushes of a brushed motor. In brushless motor elements, current and torque on the one hand and applied voltage and rotation speed (rounds per minute or RPM) may be considered to be linearly related. Brushless motors may allow for a preferred direct drive behavior of the motor element and the motor assembly respectively.

According to a further exemplary embodiment of the present invention, the motor arrangement may be adapted to assist the movement of the second structural element by at least partly decreasing perceived moving resistance of the second structural element, in particular relative to the first structural element.

Moving resistance may in particular relate to friction, manual moving force and/or unbalance of the second structural element relative to the first structural element.

It is to be understood that an actual friction, of unbalance and/or mass of the object to be moved may not be influenced per se, since these values may be provided due to physical pre-conditions, however, at least perceived friction, mass and/or unbalance of the object by a user or operator attempting to move that object may be decreased or reduced.

According to a further exemplary embodiment of the present invention, the assembly may further comprise a motion control element for controlling the movement of the second structural element relative to the first structural element.

The motion control element may in particular react to a force/torque provided to the motor element via e.g. the manual control element, thus detecting and/or determining a so produced current, from which an indication about the desired movement may be taken from or determined. The motion control element may then assist the desired movement by e.g. actuating the motor element, to assist, e.g. to move in the same direction, as the desired movement.

According to a further exemplary embodiment of the present invention, the motion control element may be operable in at least one operation mode out of the group comprising a torque mode, a current mode, a speed mode and a position mode.

In particular the torque mode and the current mode as well as the speed mode and the position mode may be combined with each other to arrive at e.g. a torque/current mode and a speed/position mode.

In the torque/current mode a desired movement may be detected while in a speed/position mode a desired position may be detected, taken up and/or subsequently held.

According to a further exemplary embodiment of the present invention, the mode of operation of the motion control element may be substantially instantaneously switchable.

In particular, the mode of operation may be substantially instantaneously switchable between a torque/current mode and a speed/position mode. This may allow for a complex movement where first a desired movement is indicated to the motion control element for arriving at a defined position with a switch to a position mode, in which the position of the second structural element relative to the first structural element is determined and subsequently, when a current position is determined that equals a desired position, the position may be upheld. The motion control element may continuously switch between a torque/current mode and a speed/position mode until a desired position has been arrived at.

According to a further exemplary embodiment of the present invention, the motor assembly may further comprise an Omega drive and/or a dual belt drive.

An according drive may allow for a simple yet effective movement of the first structural element relative to the second structural element with increased accuracy.

According to a further exemplary embodiment of the present invention, the dual belt drive may comprise a movable belt, arranged at the motor arrangement and a fixed belt, arranged at the second structural element. The movable belt and the fixed belt may be arranged for positive fit and the motor arrangement may be adapted to move the second structural element relative to the first structural element by actuating the moving belt.

An according dual belt drive may allow for a positioning with particularly increased accuracy while reducing force or tension in the belt arrangement.

According to a further exemplary embodiment of the present invention, the assembly may further comprise at least one element out of the group consisting of an absolute position determining element to determine the position of the second structural element relative to the first structural element, a force determining element, a pressure determining element, a weight determining element and an inclination determining element.

The inclination determining element may in particular be a one axis or two axes inclination determining element. Each of the determining elements may be employed for determining a parameter for influencing the movement of the motor assisted movement assembly. The respective determined parameters may in particular be employed by the motion control element for controlling the assisted movement. Parameters may be employed for the assisted movement without a user or operator noticing, thus resulting in a preferred natural manual control. Determining elements may in particular be sensors.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with the similar or identical reference numerals.

The figures are not drawn to scale, however may depict qualitative proportions.

DETAILED DESCRIPTION OF THE EMBODIMENTS

Figure 1:
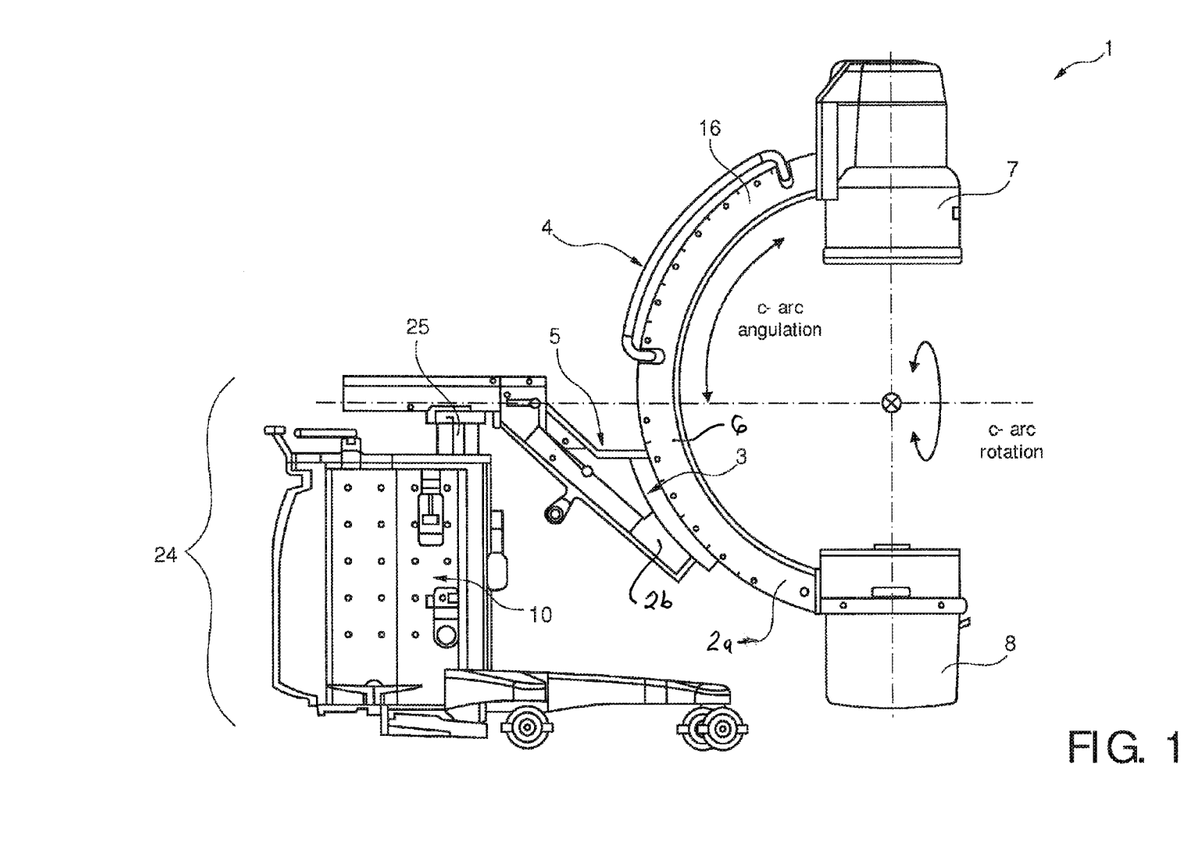
FIG. 1 shows an overview of an exemplary embodiment of a C-arc system according to the present invention.

Now referring to FIG. 1, an overview of an exemplary embodiment of a C-arc system according to the present invention is depicted.

A C-arc X-ray system 1 comprises an X-ray generating device 8, e.g. an X-ray tube, and an X-ray detector 7 oriented towards each other and operatively coupled for the generation of an X-ray image of an object. Both the X-ray generating device 8 and the X-ray detector 7 are arranged at a C-bow element 16. On the C-bow element 16, a manual control element 4, in FIG. 1 exemplary depicted as a handgrip or handrail, is arranged. In FIG. 1, the C-bow element 16 may be considered to constitute a second structural element 6, whereas the body of the C-arc system 1 may be considered to constitute a first structural element 5. A motor arrangement 3 is arranged at the junction between the first structural element 5 and the second structural element 6, e.g. between the body 24 of the X-ray system 1 and the C-bow element 16. The body 24 may comprise a further moving element 25, in FIG. 1 exemplary arranged for raising and lowering the C-bow element 16.

The body 24 further comprises the motion control element 10, which is operatively coupled with actuators or motors arranged at the moving element 25 and the junction between the first structural element 5 and the second structural element 6 and further may control the X-ray generating device 8 and the X-ray detector 7 for the generation of X-ray images.

The C-arc system 1 according to FIG. 1 may in particular be understood as a mobile X-ray system for surgical applications. The C-bow element 16 may rotate over two axes, angulation and rotation. Together with the moving element 25 for adjusting the height and the longitudinal movement capability of the mobile X-ray system 1 by rolling the whole X-ray system 1 on the floor of e.g. an operating room, an object is placeable in the isocentre, i.e. the intersection of the rotation and angulation axis.

Even when a user changes the projection angle by rotating or angulating the X-ray generating device 8 and the X-ray detector 7 about the object 9 to be examined, the point of interest of the object will stay in the centre of the image. Depending on a specific image acquisition application, the user may decide to perform a dual axis or a single axis movement by using manual control element 4. In case only a single axis movement is desired, the undesired axis may be blocked. For the following description, the motor element is moving the C-bow element 16 in an angulation movement.

An operator is employing manual control element 4 to provide an indication of a desired movement, e.g. turning the C-bow element 16 counterclockwise. The operator may thus pull the manual control element 4 downwards, in direction of the floor of the operating room, consequently indicating to the motion control element 10 a desired counterclockwise rotation.

The motor arrangement 3 together with the motion control element 10 determines that an indication for a desired movement is present and consequently the motion control element 10 signals the motor arrangement 3 to support or assist the desired movement by actuating the motor element 3a for a movement in the same, here counterclockwise, direction. Thus, the operator is substantially only required to provide an initial indication of a desired movement, possibly in the course of the movement upholding the indication of a desired movement by continuing to slightly force the manual control element 4 in the direction of the desired movement while the actual movement energy for moving the C-bow element 16 counterclockwise or at least a part thereof is provided by the motor arrangement 3, in particular the motor element 3a.

Figure 2:
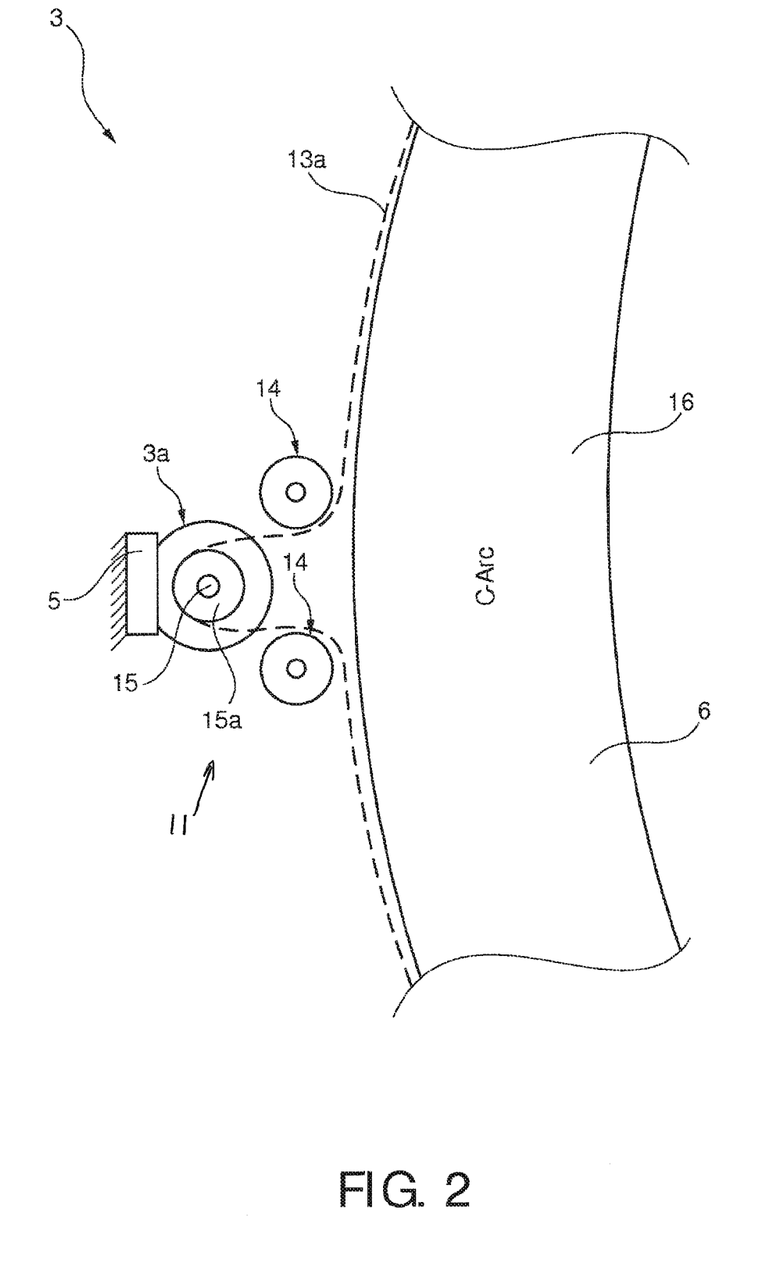
FIG. 2 shows an overview of an exemplary embodiment of a drive unit of the C-arc system of FIG. 1.
Figure 3:
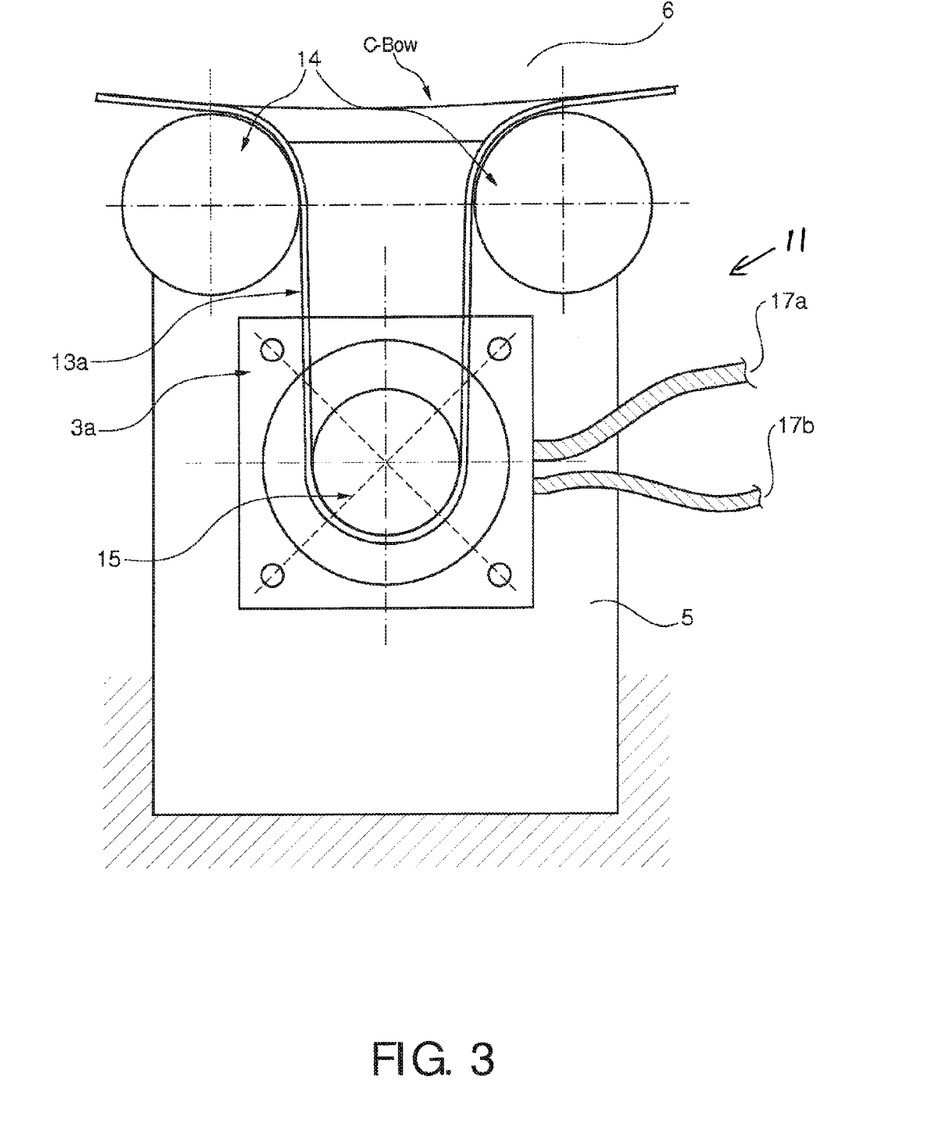
FIG. 3 shows a detailed view of an exemplary embodiment of an Omega drive according to the present invention.

Now referring to FIGS. 2 and 3, an overview of an exemplary embodiment of a drive unit of the C-arc system 1 of FIG. 1 and a detailed view of an exemplary embodiment of an Omega drive 11 according to the present invention are depicted.

FIG. 2 shows the basic operating principle of a motor arrangement 3 for motor assisted moving of the bow 16 in the angulation direction, thus clockwise or counterclockwise with regard to FIG. 1.

The C-bow element 16 comprises a belt 13a attached to its ends, which runs along the outer circumference of the C-bow element 16 until reaching, seen from each end, a guide wheel 14. The outer circumference of the guide wheels 14 are arranged at a distance substantially equal to the outer circumference of a toothed wheel 15a arranged at the motor element shaft 15.

The toothed wheel 15a may be a separate element attached to the motor element shaft 15 or may be an integral part of the motor element shaft 15. Due to the aforementioned distance of the guiding wheels 14 from one another, the toothed belt 13a is deflected substantially perpendicular from the surface of the C-bow element 16 running around the guiding wheels 14 to the motor element shaft 15 and its toothed wheel 15a.

The guiding wheels 14 regularly have an even surface for a preferred smooth running of the toothed belt 13a around them. The side of the toothed belt 13a arranged at or around the guiding wheels 14 is substantially flat, while the surface of the toothed belt 13a that is situated next to the surface of the C-bow element 16 and the toothed wheel 15a of the motor element shaft 15, respectively, is arranged in a toothed fashion, comprising tooth and gaps between the tooth or indentations between the toothed elements of the toothed belt 13a.

The toothed elements of the tooth belt 13a are substantially of rectangular shape and are adapted to match teeth incorporated into the toothed wheel 15a of the motor element shaft 15, consequently providing a positive fit or positive locking of the teeth of the toothed belt 13a and the teeth of the toothed wheel 15a.

The motor element 3a is arranged and attached to a first structural element 5, which may be seen as being substantially connected to the floor of the OR, e.g. by a stand or body 24. Now, when the motor element 3a is rotating the motor element shaft 15, thus rotating the toothed wheel 15a, due to the positive fit of the toothed wheel 15a and the toothed belt 13a, the belt 13a is moved along, over the surface of the toothed wheel 15a, thus the C-bow element 16 is turned clockwise or counterclockwise with regard to FIG. 1.

Thus, the C-arc 1 is driven with a toothed belt 13a, which is fixed at both ends of the C-arc 1 with its teeth arranged over the outer diameter or surface of the C-bow element 16. The motor element 3a with its toothed wheel 15a is mounted at the first structural element 5 in the junction between the first structural element 5 and second structural element 6, in FIG. 2 of the C-bow element 16.

The guiding wheels 14 guide the belt over the toothed wheel 15a. At one side of the C-arc 1 a fixation may be provided as a tension, thus providing adequate tension of the toothed belt 13a for highly accurate movement free of play. The efficiency of an according Omega drive and also a respective dual belt drive is sufficiently high, so that the drive system may be considered to constitute a direct drive.

The influence of the motor element 3a, when not energized, e.g. during manual control in clutch operation mode, the additional force for movement may be neglected.

The necessary control force for a user or an operator is caused by friction, inertia and some remaining unbalance. These forces, while not being comfortable and possibly too high for rapid movement, may still be considered to be acceptable for use without a motor assist.

A motor assist function according to the present invention will make the manual control lighter and easier by adding a fraction of the necessary forces to the load. The user may still feel friction and inertia, only with a reduced level. Unbalance may be compensated for completely.

FIG. 3 depicts the Omega drive of FIG. 2, however further depicting an encoder cable 17b for receiving a feedback from the motor regarding the torque acting on the motor element 3a or for determining a position, in particular an absolute position of the motor element 3a, which may be e.g. a brushless motor element 3a. Power is supplied to the motor element 3a via cable 17a.

Figure 4:
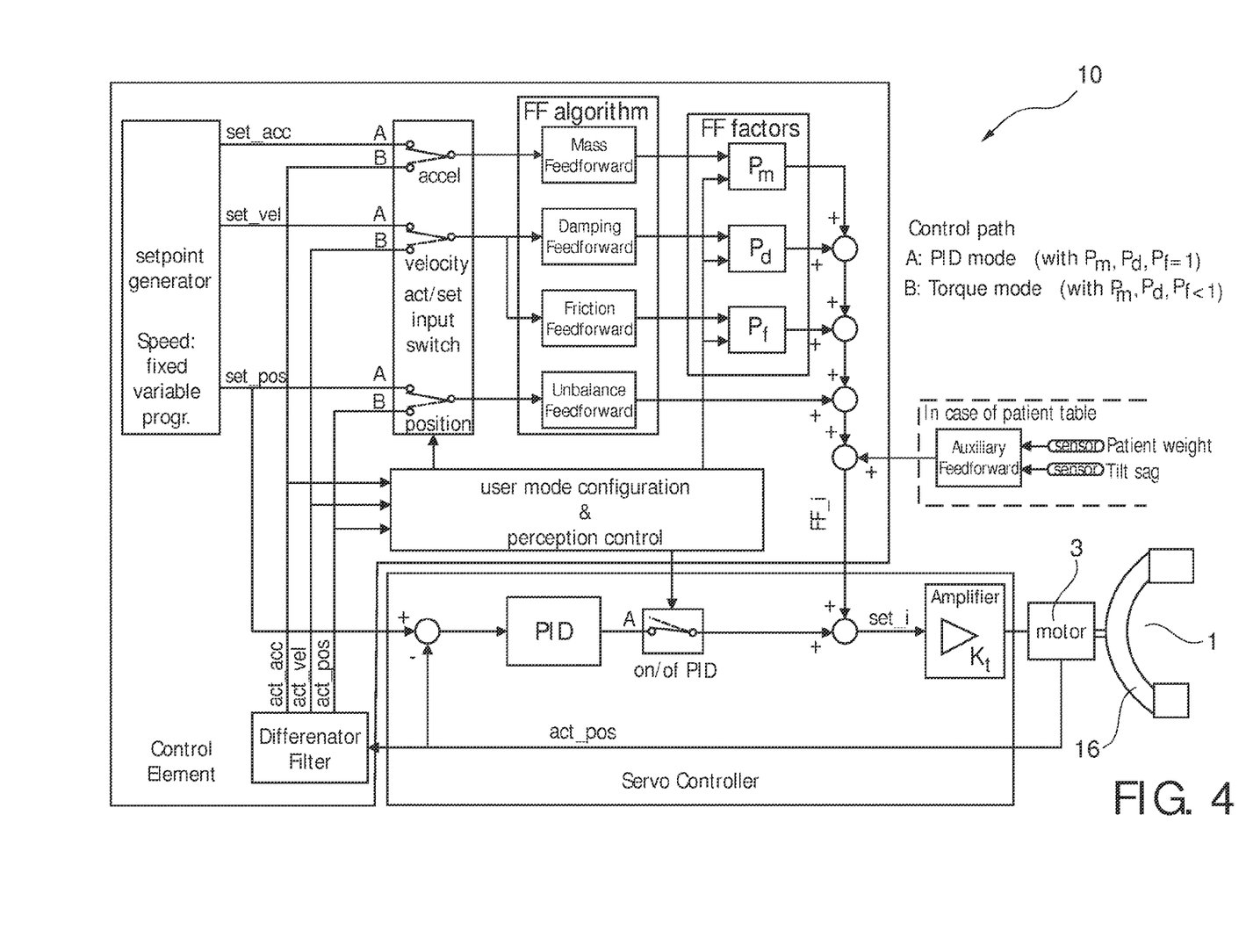
FIG. 4 shows a schematic of an exemplary embodiment of the motion control element of a motor assisted movement assembly according to the present invention.

Now referring to FIG. 4, a schematic of an exemplary embodiment of the motion control element of a motor assisted movement assembly according to the present invention is depicted.

The motor arrangement 3 may e.g. be a brushless AC, vector controlled motor arrangement 3 for the actuation of the C-arc X-ray system 1. A brushless AC (BLAC) motor may in particular employ an electronically-sinusoidal vector controlled commutation system. An according type of motor may provide for a continuous four-quadrant torque and speed range starting from zero.

The motor element 3a receives an actuating power via amplifier $K_t$ and provides a feedback regarding its position by an absolute position feedback encoder for commutation and servo control. In FIG. 4, two basic modes may be set, described as mode A, the PID or position mode, and the mode B, the torque/current mode. The servo controller provides functions like brushless AC commutation control, torque/current control loop, position (PID) control loop and "on the fly" control loop switching mechanism.

The Amplifier may provide the electronic commutation and the current loop. Due the motor torque possibly being proportional (Kt) with the current, a torque control may be achieved. The PID control may react on the position error to minimize it. To achieve this, the PID controller may deliver a proportional, the integral and the derivative values from the error signal. The "on the fly" mode switching may ensure that during the transition no can may be felt. This may be achieved by increasing or decreasing the three PID parameters smoothly.

The control principle is depicted by the block diagram shown in FIG. 4, which provides an overview of all the functions of the motor controller. The functions are located in a servo controller and in the control element. The amplifier provides the commutation and the control loop. A current set point is generated by the PID controllers and the feed forward offset. A motor position feedback may be provided by a high resolution absolute encoder.

In case a feed forward controlled system is provided, the set current may be determined by the feed forward algorithm, in particular depending on the position, velocity and acceleration setpoints and the mass, damping, friction and the unbalance parameters. In this case, the set current may in particular equal the offset current. The PID controller may correct deviations of the feed forward model.

In the PID mode or the position or speed control mode, switches in the "act/set input switch" element and "on/off PID" in the servo controller are set to "mode A". The feed forward algorithm may calculate or determine an expected motor current, based e.g. on a physical movement model. The model may contain parameters like friction, damping, mass and unbalance and the may refer to the respective physical formula. If the modeling matches, in particular substantially fully matches with the modeled real system, a contribution from the PID controller to the current set point to the amplifier may not be required. In this, theoretical case, the movement of the C-bow element 16 may follow a requested or desired trajectory without the support of the PID controller. An according model may also be used as a reference for the assist settings of the assist mode.

During the assist mode, the PID control is switched off and the movement set points are substituted by actual set points from the differenator filter, as opposed to the PID mode where the respective values are provided by the set point generator. In the assist mode, the feed forward mechanism may stay active, but the amount may be reduced to a required assist level. In the assist mode, the unbalance feed forward may be added completely. A damping contribution may be employed to avoid too high a manual speed by e.g. providing a counteracting force, which may result in substantially reducing the mechanical motor output or assisted movement or even counteracting or even opposition, in which case Pd may be even below zero.

With perception parameters or factors $P_m$, $P_d$ and $P_f$, the required or desired assistance may be adjusted. In assist mode, these parameters may be between 0 and smaller than 1, while in PID mode the parameters may be equal to 1. The allowable range of the factors is between 0 and 1 with both margins included. The actual speed and acceleration is acquired by differentiation and filtering of the actual position feedback, which is performed in the differenator filter. A movement may in particular be activated when the motion controller detects a position deplacement.

Also, preferred positioning may be implemented. By using the assist mode, stopping in pre-programmed positions may be implemented. A user provides a manual indication of a desired direction of movement, in which direction a programmed position may be situated. Near this position, the control may be automatically overruled by the PID position controller to force a smooth and precise stop and the pre-programmed position. The user mode controller provides a smooth control mode switching from current loop to PID loop. After the movement is stopped, the assist mode may again be available.

Furthermore, a break mode may be implemented, which substantially equals a stop at a preferred position, like described earlier. Also, a hold/break function may be realized by keeping a position in PID mode with the motor only being activated when the break position is left.

The control element of FIG. 4 comprises a further auxiliary feed forward component, in case e.g. a patient table is to be controlled also or in case position information of a patient table is to be taken into account as well.

The auxiliary feed forward input may be used for compensation of further force disturbances by external influences, like e.g. tilting of the system or a variation as of the object to be examined. The compensation may in particular be performed at a patient support or patient table as will be described later with reference to FIG. 9.

Figure 5:
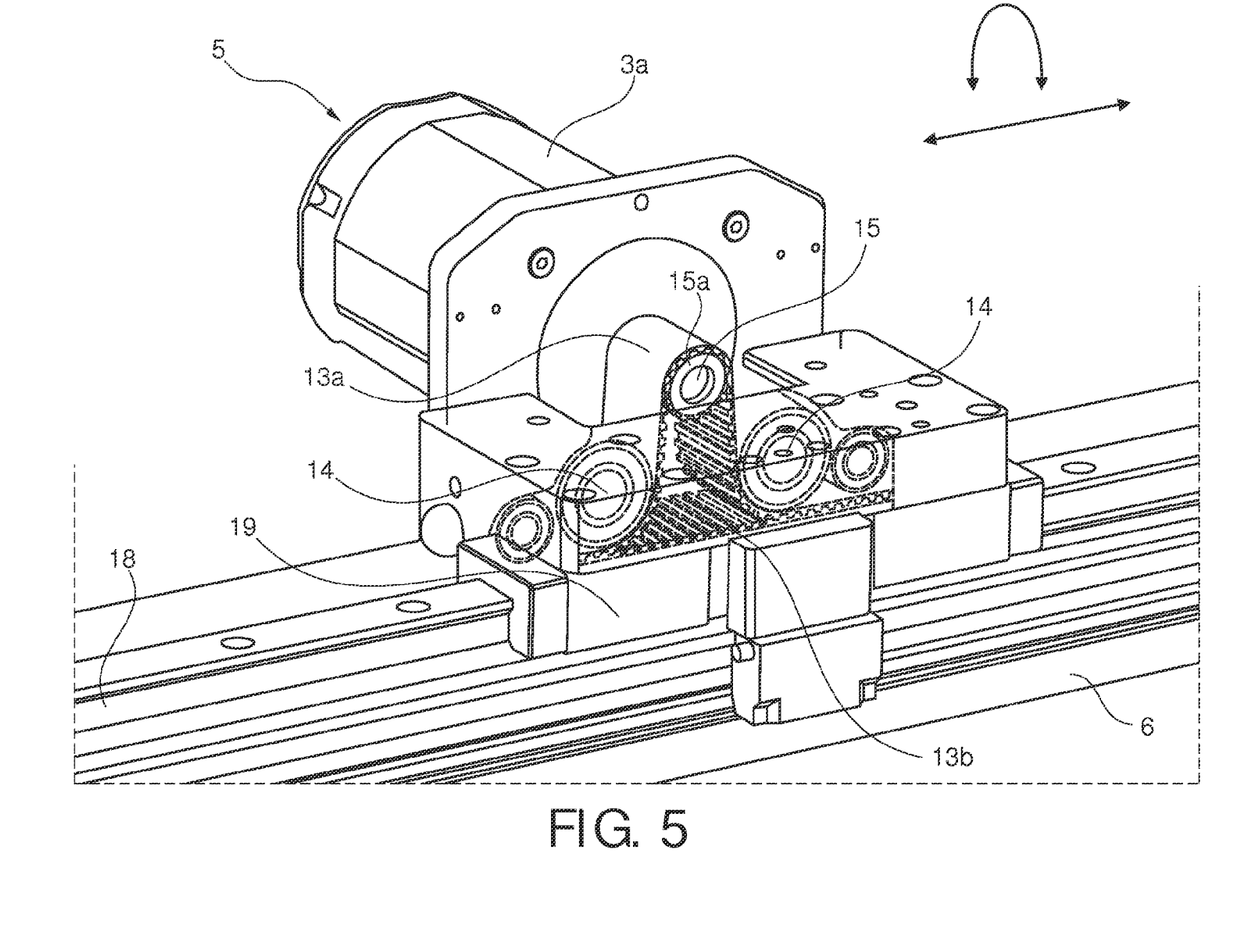
FIG. 5 shows a detailed view of an exemplary embodiment of a linear dual belt drive according to the present invention.

Now referring to FIG. 5, a detailed view of an exemplary embodiment of a linear dual belt drive 12 according to the present invention is depicted.

In FIG. 5, a dual belt drive arrangement 12 is depicted, here as a linear axis drive. The main difference to an Omega drive 11 as described earlier may be seen as the addition of a second toothed belt 13b substantially over the full operating length of the drive arrangement. Both toothed belts 13a, 13b, also referred to as timing belts, are in positive locking or teeth to teeth mating over the whole movement range except for the distance or space between the two guiding wheels 14, where the toothed belt 13a is wound around the toothed wheel 15a of the motor element shaft 15.

An according drive arrangement may allow for a substantially tension-free toothed belt 13a in the region from the guiding wheels 14 to the end of the movement range with a force or tension only existing in the belt 13a in the small zone between the two guiding wheels 14 and the toothed wheel 15a. With an according dual belt drive 12, the motor element 3a to which the first structural element 5 may be attached to, may be moved about the second structural element 6. For an easy and relatively friction-free movement, a guiding element 18 is attached to the second structural element 6 and a guided element 18 is attached to motor element 3a, thus the first structural element 5 being situated underneath the toothed belts 13a,b in FIG. 5 to allow a linear movement.

In the case of FIG. 5, a sideways movement of the guided element 19 relative to the guiding element 18 is induced by the rotation of the motor element 3a, in particular the motor element shaft 15 with the toothed wheel 15a. With an according rotational movement of the toothed wheel 15a, the toothed belt 13a is pulled towards the motor element 3a on one side of the toothed wheel 15a while being pushed away from the motor element 3a on the opposing side, with the sides depending on the rotation direction. This movement is deflected by the guiding wheels 14 to arrive at a sideways movement induced by an up/down movement of the toothed belt 13a, thus the rotational movement of the toothed wheel 15a. In case a movement of the second structural element 6 towards the right side of FIG. 5 is intended, the toothed wheel 15a may rotate clockwise, in case a fixed position of the first structural element 5 is assumed.

Figure 6:
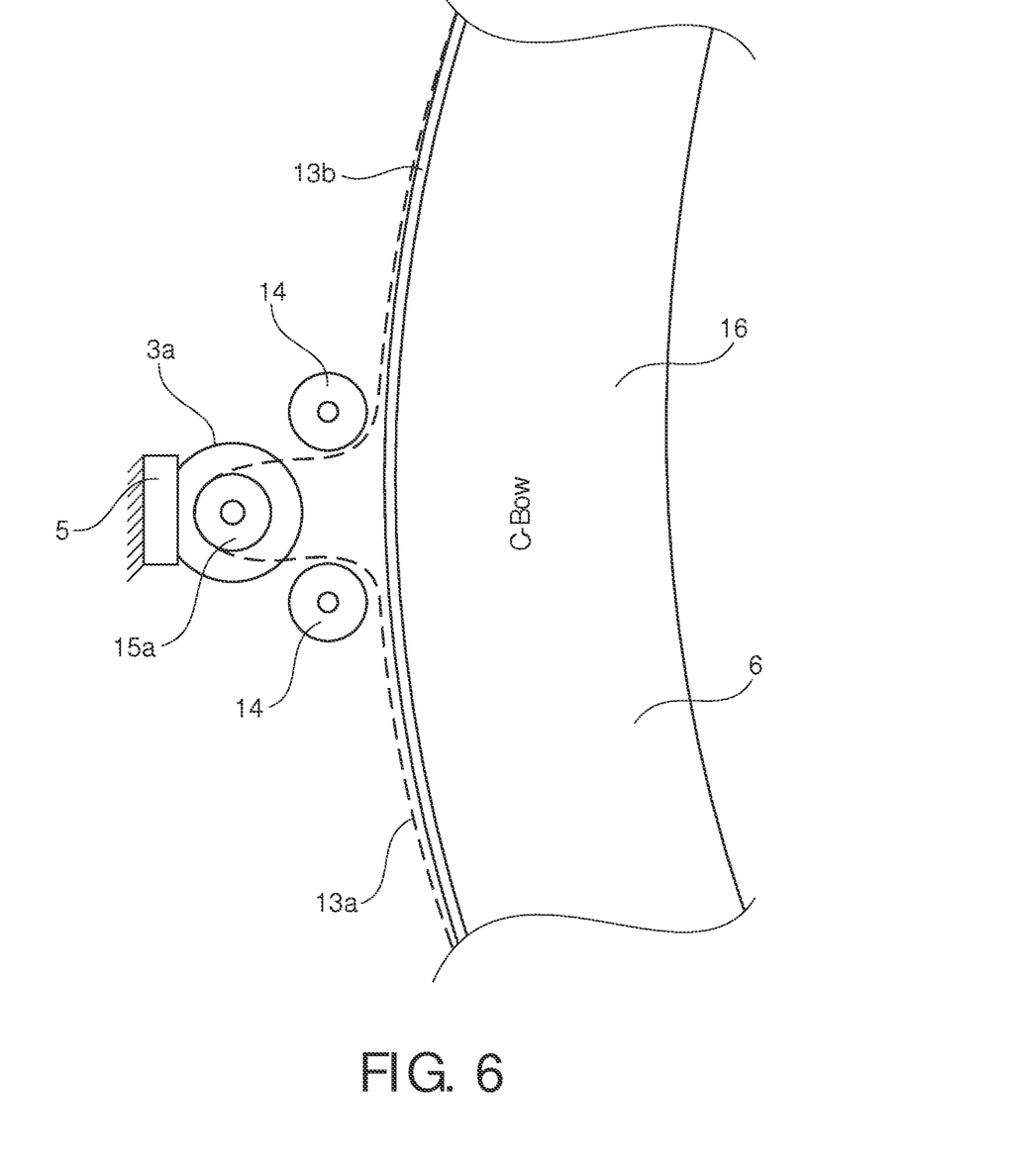
FIG. 6 shows an overview of an exemplary embodiment of a dual belt drive arranged at a C-arc system according to the present invention.

Now referring to FIG. 6, an overview of an exemplary embodiment of a dual belt drive arranged at a C-arc system according to the present invention is depicted.

In FIG. 6, the dual belt drive 12 is adapted to provide an angulation rotation movement of the C-bow element 16 with regard to FIG. 1. A toothed belt 13b may be attached substantially over the whole outer circumference of the C-bow element 16. The toothed belt 13b may be attached to the C-bow element 16 substantially over its full length or, due to the curvature of the C-bow element surface may only be attached at its respective end points. A second toothed belt 13a, or mating belt is situated directly above the toothed belt 13b, with the teeth of the belt facing each other, possibly being in positive fit from the guiding wheels 14 to the respective ends of the C-bow element 16.

Between the guiding wheels 14, the toothed belt 13a is wound around the toothed wheel 15a of the motor element 3a. Similar to the linear axis drive of FIG. 5, a relatively small capacity timing belt may be situated on the back of the C-bow element 16, e.g. bonded to the outer surface of the C-bow element 16, with another belt 13a being in teeth to teeth mating with the toothed belt 13b. Both belts, the bonded belt 13b and the floating belt 13a, are fixed at the respective ends of the C-bow element 16, however with no or at least reduced pretension. Toothed belt 13a loops around the toothed wheel 15a of the motor element 3a similar to the Omega drive of FIGS. 2 and 3.

Figure 7:
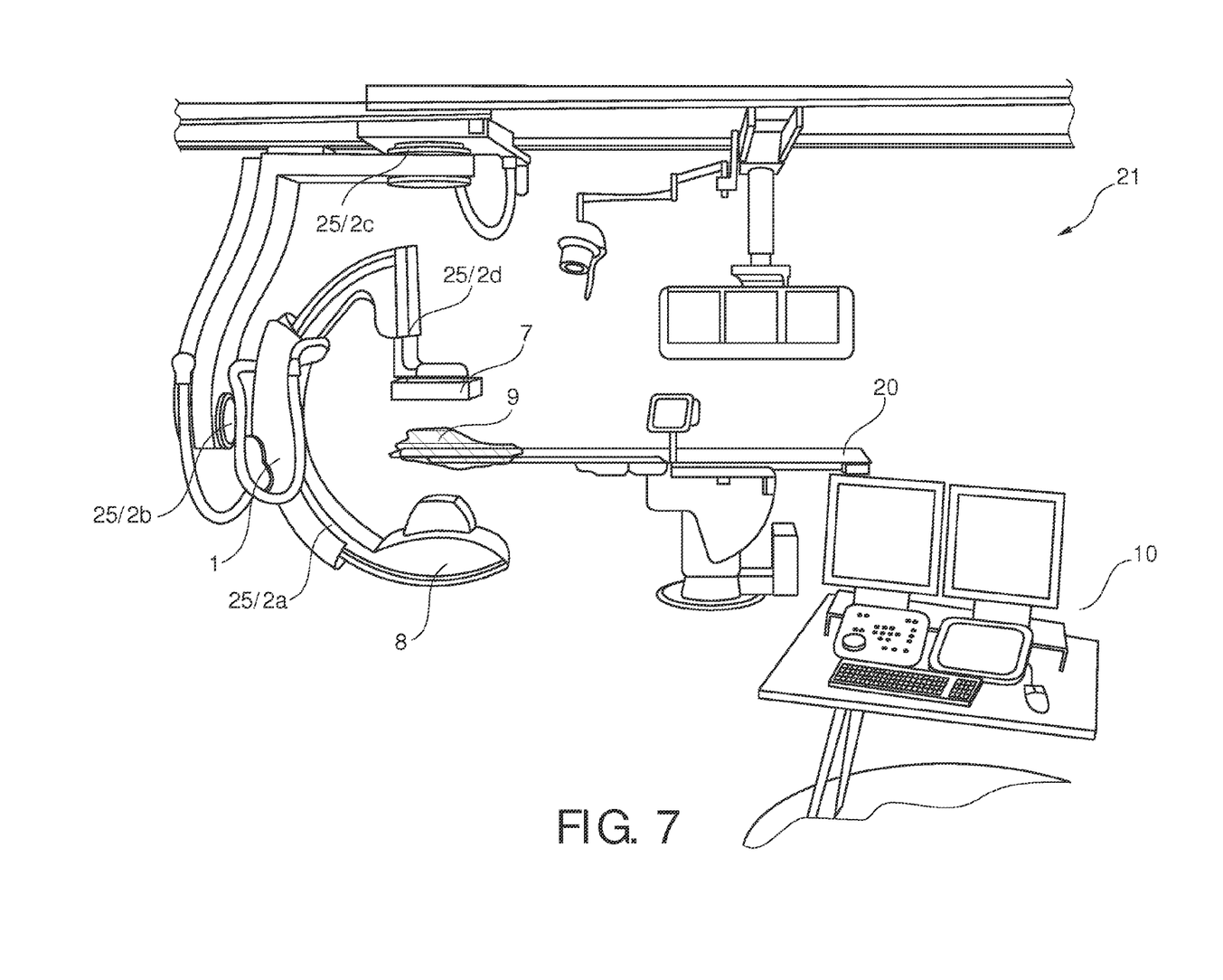
FIG. 7 shows an overview of an exemplary embodiment of an X-ray system according to the present invention.

Now referring to FIG. 7, an overview of an exemplary embodiment of an X-ray system according to the present invention is depicted.

The X-ray system 21 comprises a ceiling mounted C-arc X-ray system 1, comprising an X-ray generating device 8 and an X-ray detector 7. On a patient support 20, an object 9 is arranged at the isocentre or at least in the path between the X-ray generating device 8 and the X-ray detector 7.

The X-ray system 21 is controlled by a motion control element 10, possibly further controlling imaging parameters.

The ceiling mounted C-arc X-ray system 1 comprises multiple moving elements 25, which are implemented as motor assisted movement assemblies 2a to 2d. The motor assisted movement assembly 2a may provide a movement for C-arc angulation while motor assisted movement assembly 2b may provide C-arc rotation, with regard to FIG. 1.

Motor assisted movement assembly 2d may provide for a variation in distance between the X-ray generating device 8 and the X-ray detector 7. The motor assisted movement assembly 2c may allow for a two-dimensional linear movement of the C-arc X-ray system 1 substantially parallel to the ceiling, i.e. the ceiling support structure of the C-arc X-ray system 1 and may also provide a further rotational movement capability around an axis substantially perpendicular to the ceiling or ceiling support structure. A further movement capability for adjusting the height of the C-arc X-ray system 1 with respect to the patient support 20 may be implemented in either motor assisted movement assembly 2c or 2b.

Furthermore, the patient support 20 may provide a height adjustment. All moving elements 25 or motor assisted movement assemblies 2a to 2d may be manually controlled by a user or may be automatically operable by the motion control element 10.

Figure 8:
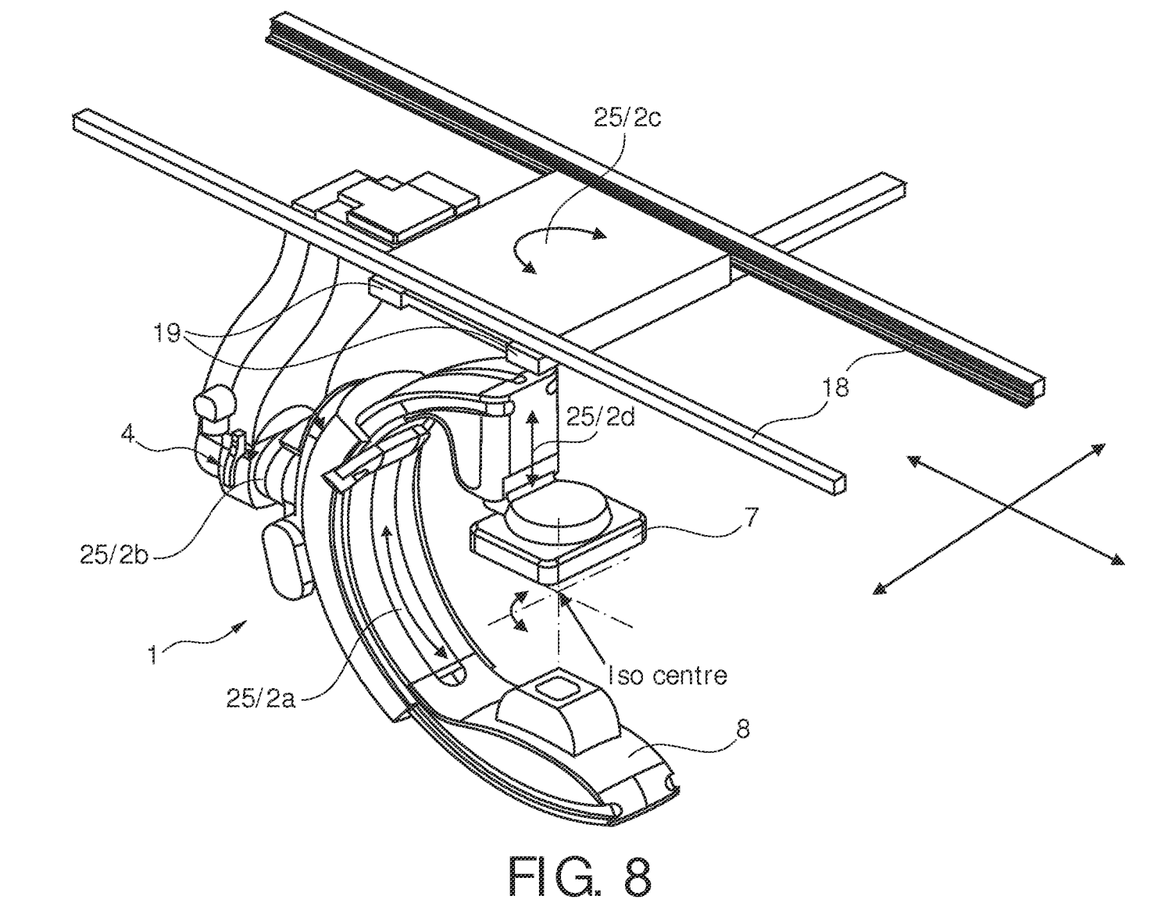
FIG. 8 shows a detailed view of the image generating part of the X-ray system according to FIG. 4.

Now referring to FIG. 8, a detailed view of the image generating part of the X-ray system according to FIG. 4 is depicted.

The C-arc X-ray system 1 of FIG. 7 comprising the X-ray generating device 8 and the X-ray detector 7 is displayed from a different angle. A respective freedom of movement of each moving element 25 or motor assisted movement assembly 2a to 2d is depicted also.

Manual control element 4 may in particular influence motor assisted movement assembly 2c for translatory and rotary movement. Further manual control elements may be provided for assisted movements with motor assisted movement assemblies 2a, 2b and 2d however are not being depicted in FIG. 8.

The C-arc X-ray system 1 may be moved, e.g. by rails mounted to the ceiling in longitudinal direction, possibly providing a two-dimensional movement parallel to the ceiling of the OR. It may be either motorized movable or be manually controlled. An exemplary C-arc X-ray system 1 may regularly weigh more than 1000 kg, thus a necessary handling force in pure manual, unassisted mode may be extremely high.

Consequently, a motor assisted movement assembly may be beneficial. In this implementation, C-arc X-ray system 1 may be mounted to guided elements 19, which may move along guiding elements 18. Toothed belts 13a,b may be attached to the ends of the guiding elements 18, e.g. rails being adapted to match the guided elements 19, e.g. a longitudinal carriage. The remaining movement capabilities, in particular the motor assisted movement may be considered to be as previously described.

Figure 9:
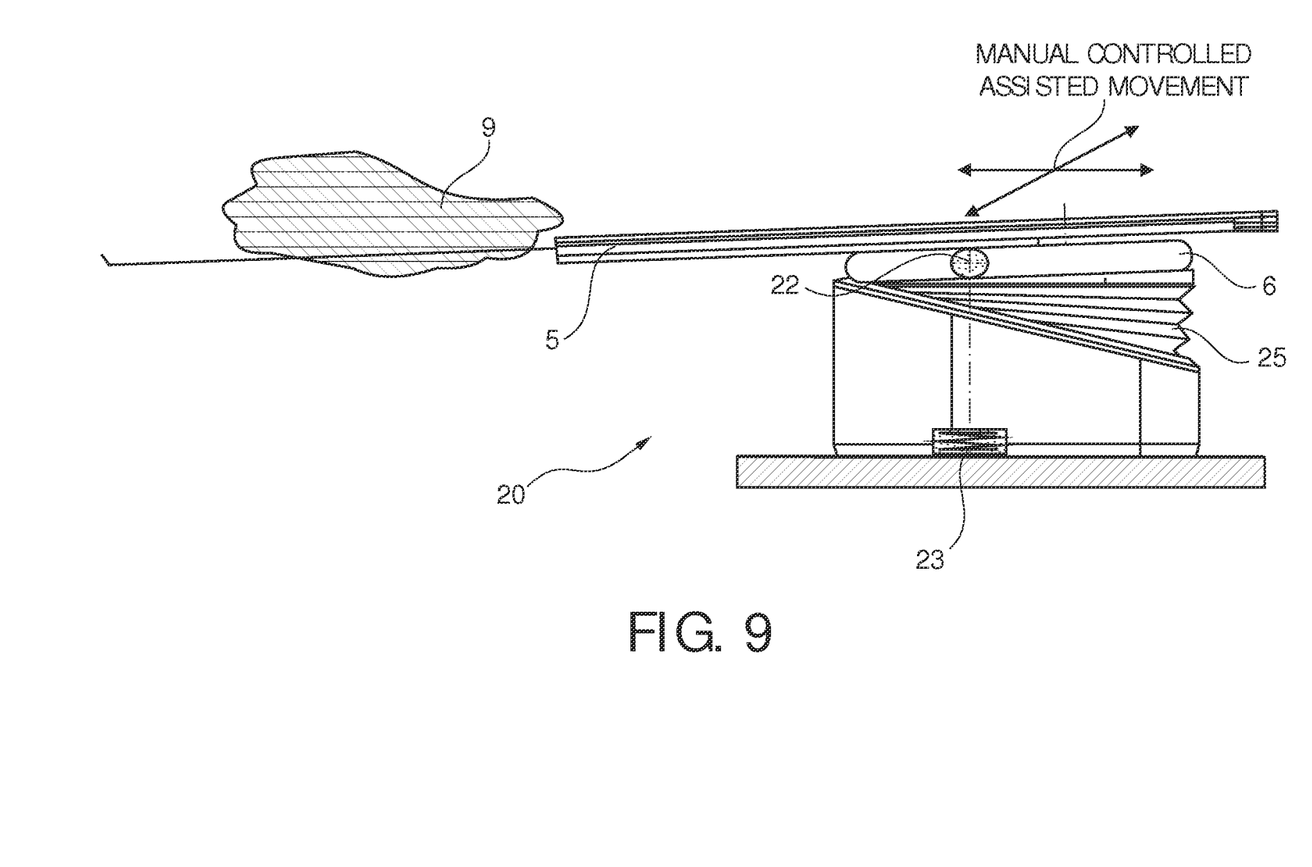
FIG. 9 shows an overview of an exemplary embodiment of a patient support according to the present invention.

Now referring to FIG. 9, an overview of an exemplary embodiment of a patient support according to the present invention is depicted.

In FIG. 9, a patient support 20 comprises an inclination determining element 22, adapted to determine inclination in one or two axes and a force, pressure or mass determining element 23, e.g. a weight sensor. An object to be examined 9 is situated on a movable patient bed which may be moved in two dimensions as depicted by the two crossing arrows which denote directions of manually controlled assisted movement for which a corresponding moving element 25 is shown.

The table top of patient support 10 may float manually in longitudinal and traversal direction. Due to the stiffness of the table base, tilt sag may occur at extended table top positions, in particular when combined with heavy objects 9 to be examined, resulting in an unbalanced force in longitudinal direction.

However, for certain medical interventions, precise positioning is mandatory. The manually controlled assisted movement may compensate for tilt sag and may reduce friction and mass forces related to a patient support 20 as well.

The longitudinal and/or transversal movement of the patient table may be compared to that of the C-arc X-ray system 1 of FIGS. 7 and 8, except for an additional unbalance situation due to the weight of the object 9. The unbalance force may be determined by a tilt angle, determined by the inclination determining element 22, and the mass of object 9, determined by force sensor 23.

The angle determining element 22 or angle sensor may measure the declination relative to the horizontal end while the force determining element or force sensor may measure the force in vertical direction. A calculation or multiplication of mass, gravitational acceleration and the sinus of the tilt sag angle may provide the unbalance force. This value or parameter may be employed as a motor assist contribution by the auxiliary feed forward of FIG. 4. The measured mass may also be used for mass compensation. The mechanism of FIG. 9 may provide an optimal assist regardless of weight or position of the object 9 to be examined.

While in the course of the description motor element 3a may in particular be arranged at the first structural element 5 and the manual control element 4 may in particular be arranged at the second structural element 6, it is to be understood that a variation or interchange of positions is conceivable as well. In other words, motor element 3a may also be arranged at the second structural element 6 and the manual control element 4 may also be arranged at the second structural element 5.

It should be noted that the term "comprising" does not exclude other elements or steps and that "a" or "an" does not exclude a plurality. Also elements described in association with different embodiments may be combined.

It should also be noted, that reference numerals in the claims shall not be construed as limiting the scope of the claims.

REFERENCE NUMERALS

1 C-arc X-ray system
2 Motor assisted movement assembly
3 Motor arrangement
3a Motor element
4 Manual control element
5 First structural element
6 Second structural element
7 X-ray detector
8 X-ray generating device
9 Object
10 Motion control element
11 Omega drive
12 Dual belt drive
13a,b Toothed belt
14 Guiding wheels/roller
15 Motor element shaft
15a Toothed wheel
16 C-bow element
17a,b Cable
18 Guiding element
19 Guided element
20 Patient support
21 X-ray system
22 Inclination determining element
23 Force/pressure/mass determining element
24 Body
25 Moving element

The invention claimed is:

1. A motor assisted movement assembly, comprising:
a first structural element;
a second structural element;
a motion control element; and
a motor arrangement, comprising a motor that comprises a rotatable shaft;
said first structural element and said second structural element being movable relative to each other;
said motor arrangement being arranged at the first structural element;
said second structural element being configured to receive a manual indication of a desired sliding movement of said second structural element relative to said first structural element;
said motor arrangement being configured to assist the movement of said second structural element relative to said first structural element in accordance with said manual indication;
said motor producing current in accordance with rotational force on said shaft, said force being caused by said manual indication; and
said motion control element being configured for causing the produced current to be measured to yield a measurement to which the assisting is responsive.

2. The assembly according to claim 1, wherein said motor is a brushless, alternating current motor.

3. The assembly according to claim 1, wherein said motor arrangement is configured to assist the movement of said second structural element by at least partly decreasing perceived moving resistance of said second structural element.

4. The assembly according to claim 1, said motion control element being further configured for controlling said desired sliding movement of said second structural element relative to said first structural element.

5. The assembly according to claim 4, wherein said motion control element is operable in at least one operation mode out of the group comprising a torque mode in which said desired sliding movement is detected and a position mode in which a current position of said second structural element relative to said first structural element is determined and, when the current position is determined to be equal to a predetermined position, said current position determined to be equal is held.

6. The assembly according to claim 5, wherein the mode of operation of said motion control element is substantially instantaneously switchable between said torque mode and said position mode.

7. The assembly of claim 6, said motion control element being configured for continuously switching between said torque mode and said position mode until arriving at a position corresponding to said manual indication.

8. The assembly according to claim 1, said assembly further comprising, at a connection between said first structural element and said second structural element, at least one of an omega drive and a dual belt drive.

9. The assembly according to claim 8, wherein said dual belt drive comprises:
a movable belt, arranged at said motor arrangement; and
a fixed belt, arranged at said second structural element;
said movable belt and the fixed belt being arranged for positive fit;
said motor arrangement being configured to move said second structural element relative to said first structural element by actuating said movable belt.

10. The assembly of claim 1, configured to detect a torque applied to said motor arrangement, said measurement being representative of said torque, said assisting being responsive to said torque.

11. The assembly of claim 1, said motor comprising an alternating current (AC) motor, said AC motor comprising said shaft.

12. The assembly of claim 1, said-first structural element having a connection site, said second structural element having a connection location at which, at said connection site, said second structural element is connected to said first structural element, said movement being such that said connection location moves along said second structural element.

13. A method of motor assisted movement, comprising the steps of:
from motor current that results from a manual indication of a desired sliding movement of a second structural element relative to a first structural element, detecting said manual indication; and,
via a motor generating said current and according to the detected manual indication, assisting the desired movement.

14. The method of claim 13, further comprising measuring a torque applied to said motor, said measuring of said torque comprising measuring the resulting motor current, said assisting being responsive to the measured torque.

15. The method of claim 13, said first structural element having a connection site, said second structural element having a connection location at which, at said connection site, said second structural element is connected to said first structural element, said movement being such that said connection location moves along said second structural element.

16. A device for motor assisted movement, comprising:
a first structural element;
a second structural element;
a junction between said first structural element and said second structural element such that, via said junction, said second structural element is movably connected to said first structural element;
a motor arrangement comprising a motor; and
a motion control element configured for causing detection, from motor current, of a manual indication of a desired movement of said second structural element relative to said first structural element, said motor arrangement being configured for, via said motor, assisting the desired movement,
wherein said first structural element is configured so as not to move in reaction to said movement of said second structural element.

17. The device of claim 16, wherein the motor arrangement is a direct drive motor arrangement.

18. The device of claim 16, configured for employing said motor current to detect a torque applied to said motor arrangement.

19. The device of claim 16, wherein the motor arrangement is arranged at the first structural element.

20. The device of claim 19, wherein the second structural element is configured to receive said manual indication.

21. The device of claim 16, wherein the motor arrangement is configured for the assisting in accordance with the manual indication.

22. The device according to claim 16, said motion control element being further configured for controlling said desired movement, wherein said motion control element is operable in at least one operation mode out of the group comprising a torque mode in which said desired movement is detected and a position mode in which a current position of said second structural element relative to said first structural element is determined and, when the current position is determined to be equal to a predetermined position, said current position determined to be equal is held.

23. The device according to claim 22, wherein the mode of operation of said motion control element is substantially instantaneously switchable between said torque mode and said position mode.

24. The device according to claim 23, said motion control element being configured for continuously switching between said torque mode and said position mode until arriving at a position corresponding to said manual indication.

25. The device of claim 16, wherein said movement is sliding of said second structural element with respect to said first structural element.

26. The device of claim 16, wherein said movement is rotating of said second structural element with respect to said first structural element.

27. The device of claim 16, wherein said first structural element is a component of at least one of an X-ray system and a patient support system, and said second structural element is correspondingly another component of said X-ray system and/or said patient support system.

28. The device of claim 27, further comprising, for adjusting patient support, an absolute position determining element to determine a position of said second structural element relative to said first structural element, a force determining element, a pressure sensor, a weight determining element, and an inclination determining element.

29. The device of claim 16, further comprising an X-ray source and an X-ray detector, said second structural element being configured for supporting said X-ray source and said X-ray detector, said junction being disposed, along said second structural element, between said X-ray source and said X-ray detector.

30. A device for motor assisted movement, comprising:
a first structural element;
a second structural element;
a motor arrangement comprising a motor, the motor arrangement being a direct drive motor arrangement; and
a motion control element configured for causing detection, from motor current, of a manual indication of a desired movement of said second structural element relative to said first structural element, said motor arrangement being configure for, via said motor, assisting the desired movement,
wherein the direct drive motor arrangement is configured to comprise a drive operation mode in which a motor assisted movement is provided, a clutch operation mode in which a substantially free, unassisted, manual movement of said first structural element relative to said second structural element is provided, and a brake operation mode characterized by stopping, or remaining, in a predefined position.

31. A device for motor assisted movement, comprising:
a first structural element;
a second structural element:
a motor arrangement comprising a motor; and
a motion control element configured for causing detection, from motor current, of a manual indication of a desired sliding movement of said second structural element relative to said first structural element, said motor arrangement being configured for, via said motor, assisting the desired movement.

32. The device of claim 31, said first structural element having a connection site, said second structural element having a connection location at which, at said connection site, said second structural element is connected to said first structural element, said movement being such that said connection location moves along said second structural element.

* * * * *